(12) United States Patent
Oh et al.

(10) Patent No.: US 8,414,590 B2
(45) Date of Patent: Apr. 9, 2013

(54) PIVOTING INSERTION APPARATUS AND METHOD

(75) Inventors: YoungHoon Oh, Montville, NJ (US); Kevin Sichler, West Orange, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 102 days.

(21) Appl. No.: 13/086,507

(22) Filed: Apr. 14, 2011

(65) Prior Publication Data

US 2012/0265305 A1  Oct. 18, 2012

(51) Int. Cl.
*A61B 17/70* (2006.01)
(52) U.S. Cl. .................. 606/86 A; 623/17.16
(58) Field of Classification Search .......... 606/99, 606/86 A, 86 B, 279, 90
See application file for complete search history.

(56) References Cited

U.S. PATENT DOCUMENTS

| | | | |
|---|---|---|---|
| 5,299,582 A * | 4/1994 | Potts .......................... 128/846 |
| 7,497,869 B2 | 3/2009 | Justis | |
| 7,575,580 B2 * | 8/2009 | Lim et al. ...................... 606/99 |
| 7,648,507 B2 | 1/2010 | Techiera et al. | |
| 7,758,617 B2 | 7/2010 | Iott et al. | |
| 2005/0090824 A1 * | 4/2005 | Shluzas et al. .............. 606/61 |
| 2007/0173831 A1 * | 7/2007 | Abdou ........................ 606/61 |
| 2007/0225726 A1 | 9/2007 | Dye | |
| 2008/0065082 A1 | 3/2008 | Chang | |
| 2008/0077138 A1 * | 3/2008 | Cohen et al. ................. 606/61 |
| 2008/0140085 A1 | 6/2008 | Gately | |
| 2008/0306489 A1 * | 12/2008 | Altarac et al. .............. 606/99 |
| 2009/0198246 A1 | 8/2009 | Lim | |
| 2010/0036443 A1 * | 2/2010 | Hutton et al. ............. 606/86 R |
| 2010/0094422 A1 | 4/2010 | Hansell | |
| 2010/0249856 A1 * | 9/2010 | Iott et al. .................. 606/86 A |
| 2011/0022088 A1 | 1/2011 | Forton et al. | |
| 2011/0196426 A1 * | 8/2011 | Peukert et al. ............. 606/279 |
| 2011/0218581 A1 * | 9/2011 | Justis ....................... 606/86 A |

* cited by examiner

*Primary Examiner* — Eduardo C Robert
*Assistant Examiner* — Lynnsy Schneider
(74) *Attorney, Agent, or Firm* — Rahman LLC

(57) ABSTRACT

A pivoting insertion apparatus and method includes a main body comprising a shaft including a longitudinal channel cavity and a forked end coupled to the shaft; an actuator seated within the channel cavity; a hinge joint including a hinge joint main body coupled to the main body and a pair of arms coupled to the hinge joint main body; an outer sleeve including an outer shell surrounding a cavity that loosely contains the main body, actuator, and a portion of the hinge joint; a member housing including a member housing body that includes a main cavity housing the longitudinal member and a pair of arms coupled to the member housing body; and a linkage component including a first end coupled to the forked end of the actuator and a second end coupled to at least one of the member housing arms.

22 Claims, 13 Drawing Sheets

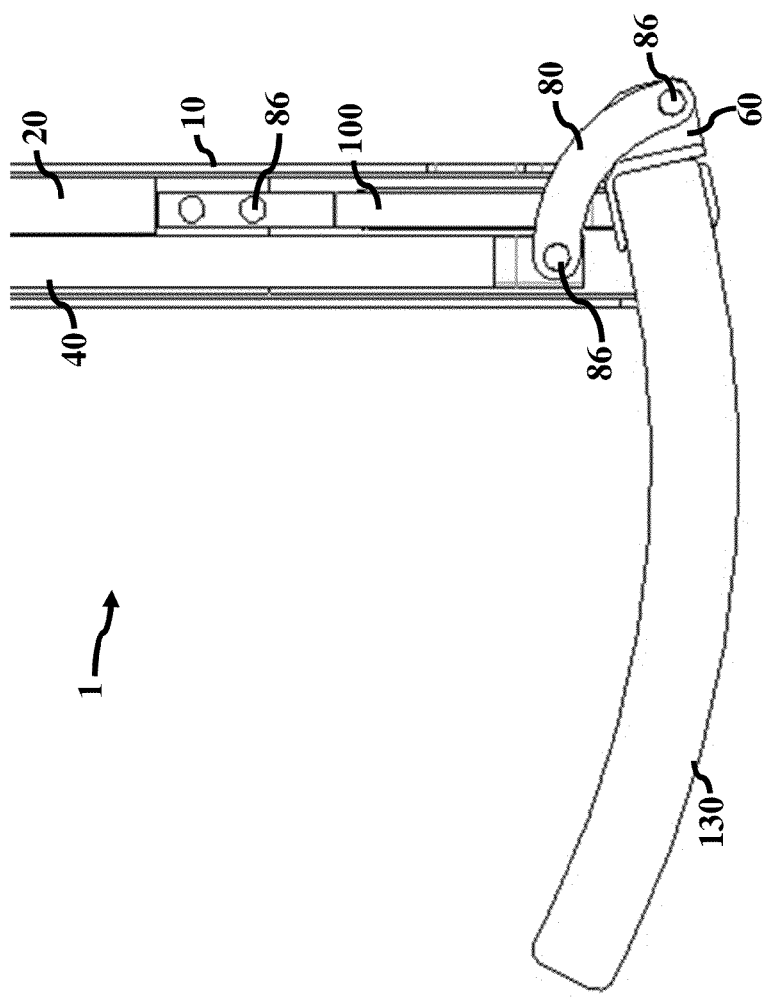
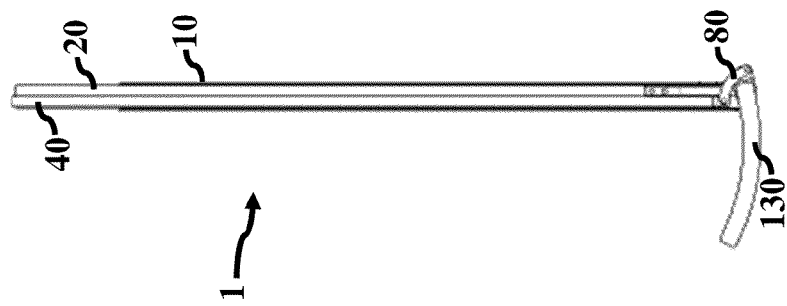

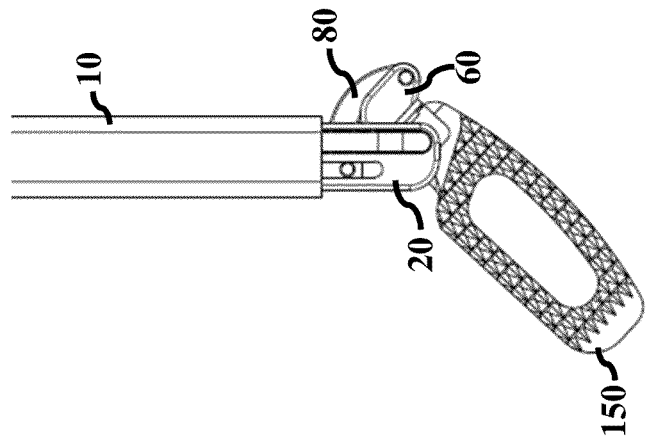
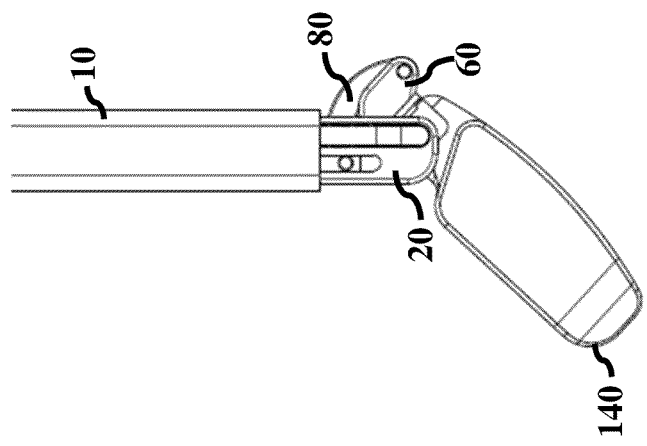
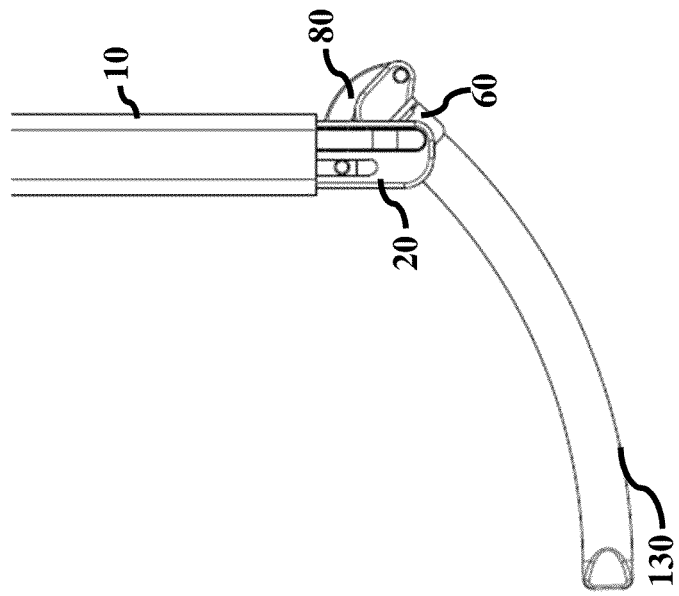

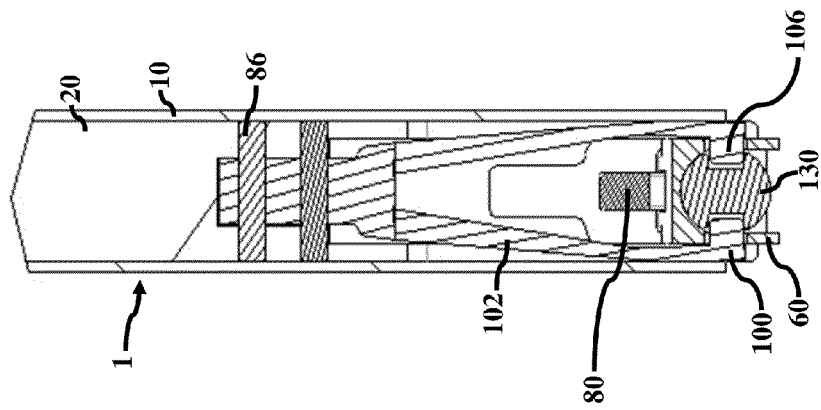
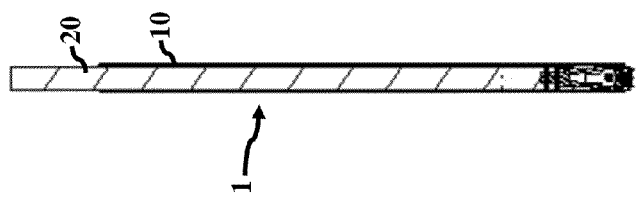
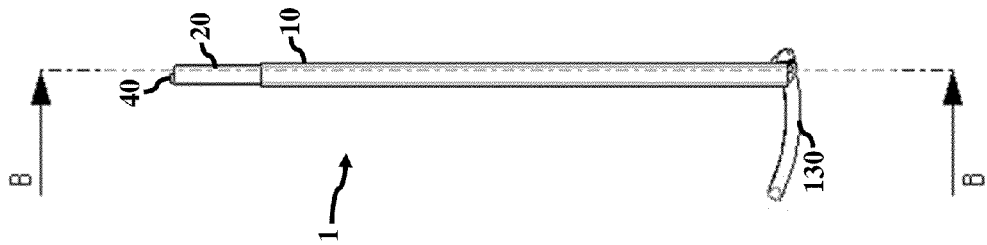

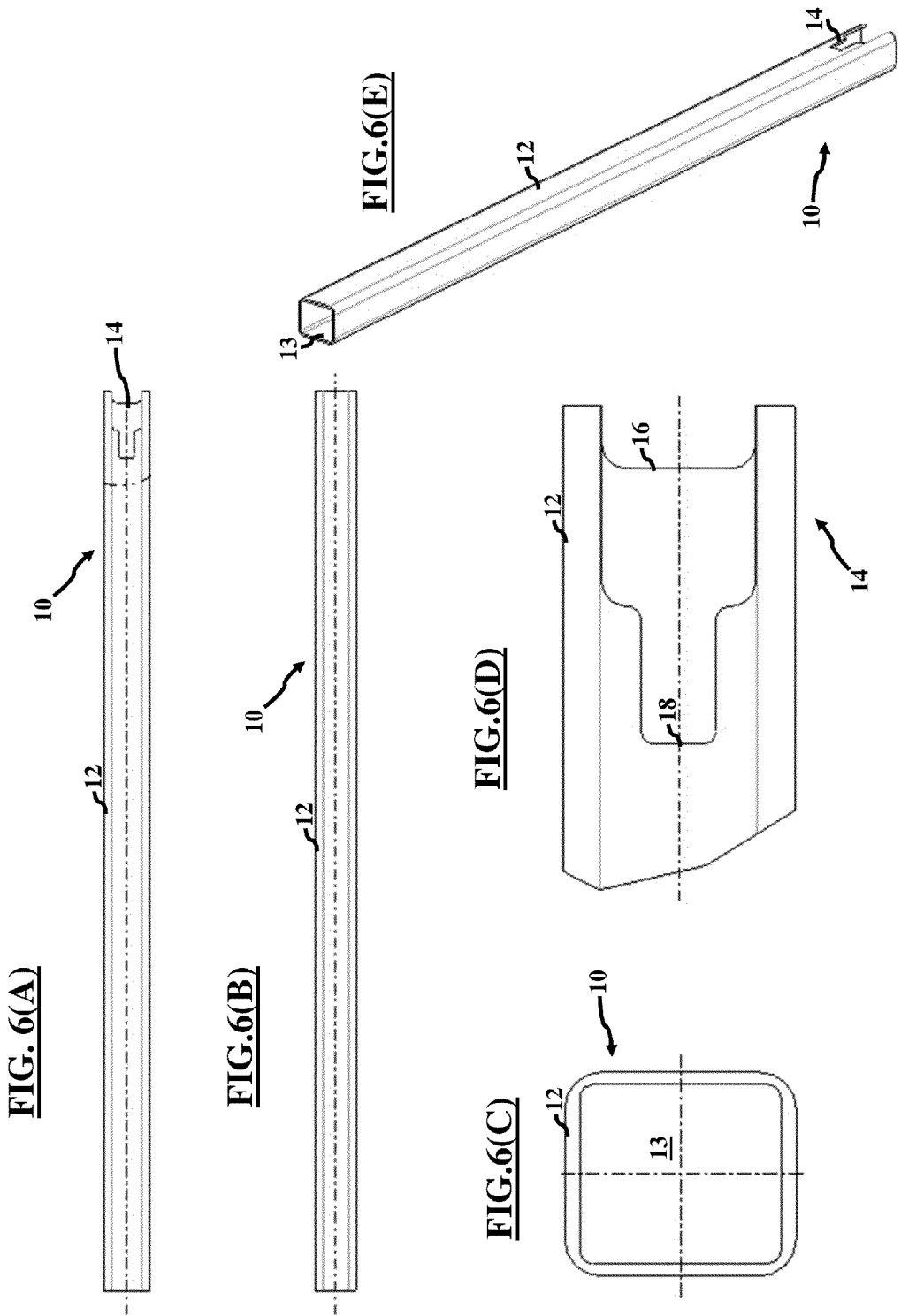

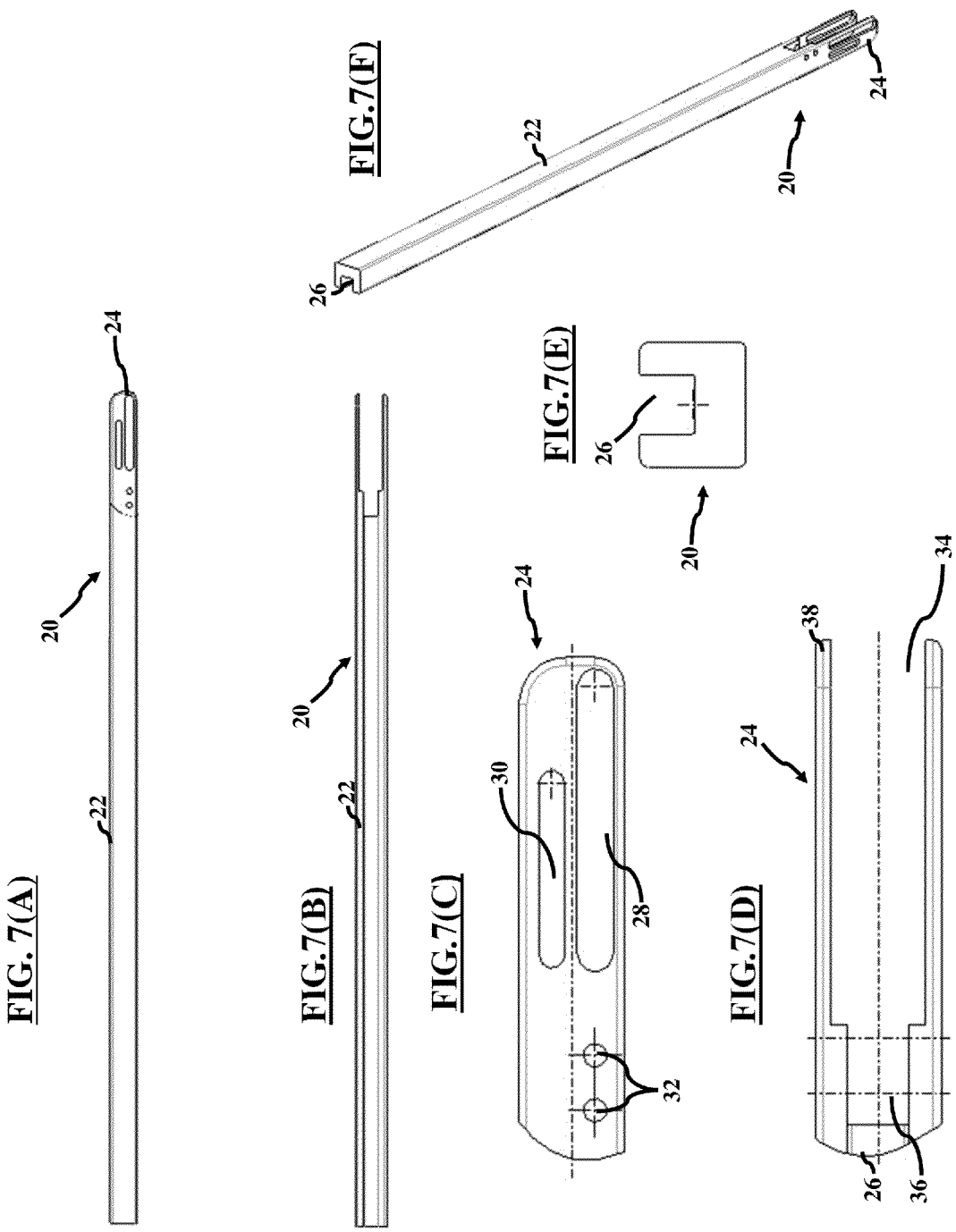

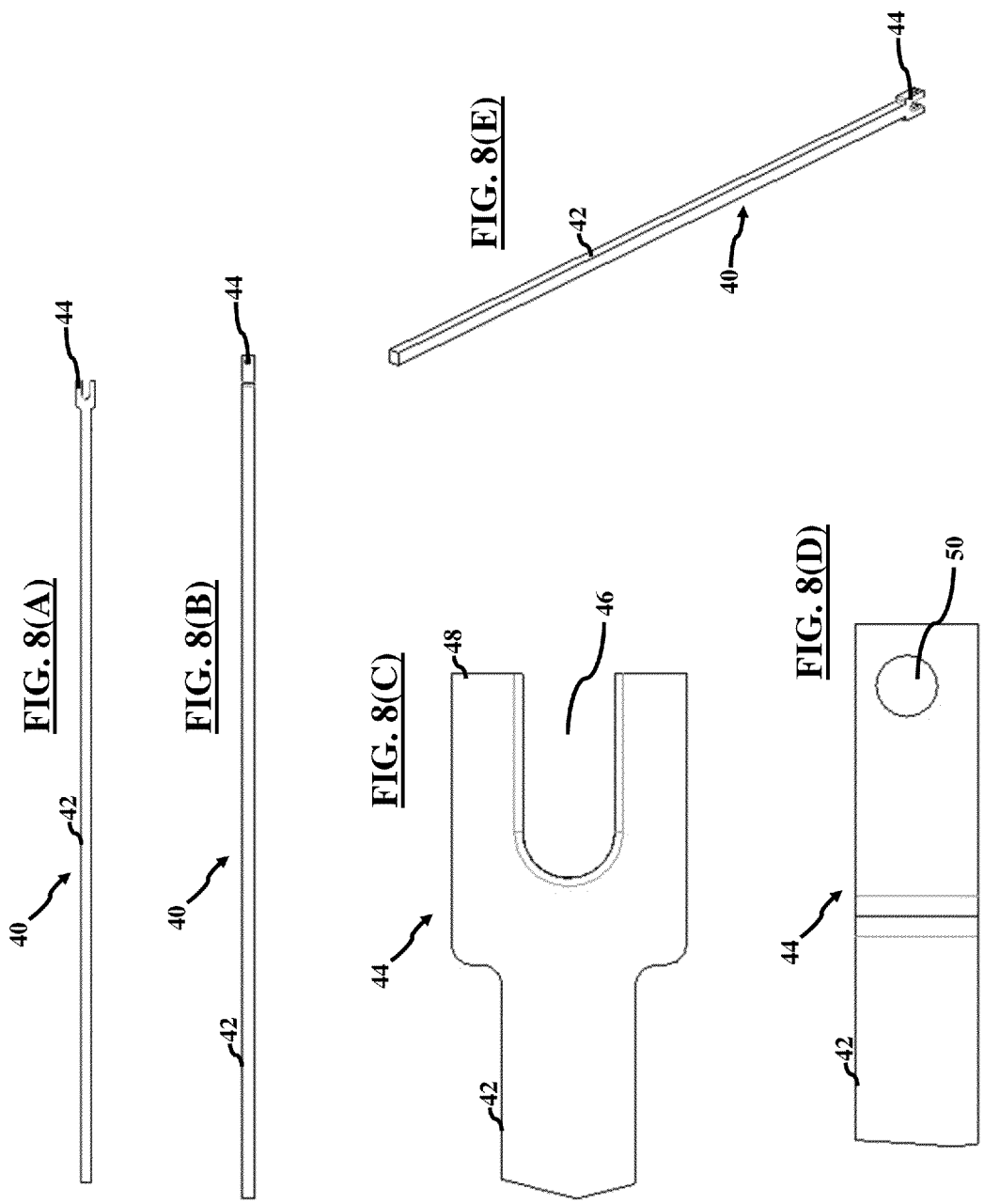

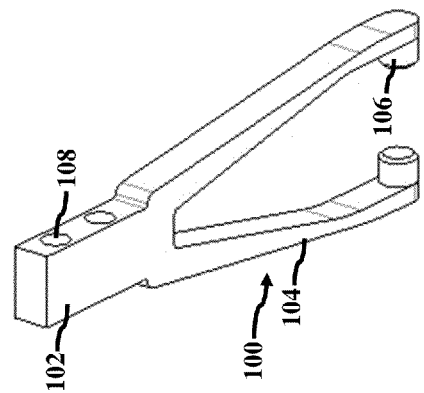
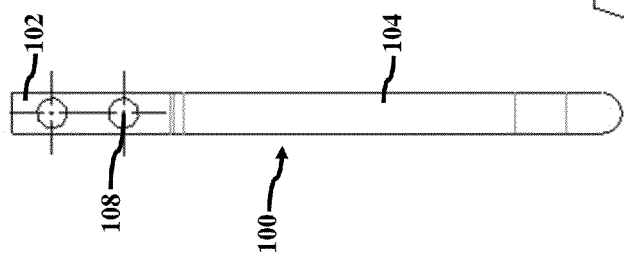
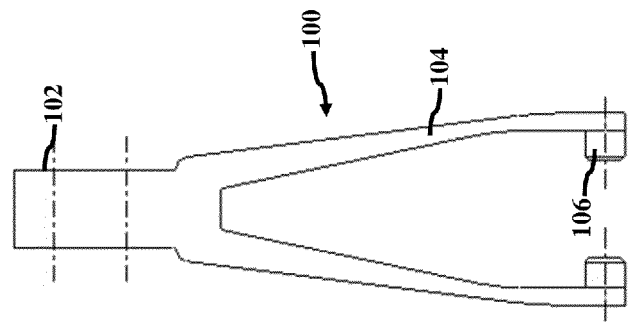
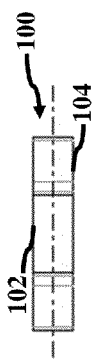

PIVOTING INSERTION APPARATUS AND METHOD

BACKGROUND

1. Technical Field

The embodiments of the invention generally relate to medical devices and assemblies, and more particularly to an orthopedic surgical implant assembly used in the field of surgical lumbar, thoracic and cervical spine treatment.

2. Description of the Related Art

Traditional surgical procedures for pathologies located within the body have historically caused significant trauma to the intervening tissues. These procedures often require a long incision, extensive muscle stripping, prolonged retraction of tissues, denervation and devascularization of tissue. Such procedures can require operating room time of several hours and several weeks of post-operative recovery time due to the destruction of tissue during the surgical procedure. In many cases, these invasive procedures lead to permanent scarring and pain that can be more severe than the pain leading to the surgical intervention.

The development of percutaneous surgical procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods. For example, conventional surgical instruments used during minimally invasive surgical procedures provide limited movement during surgery. These shortcomings to convention minimally invasive surgical instruments frequently raise the risk of additional morbidity to a patient undergoing a minimally invasive surgical procedure.

SUMMARY

In view of the foregoing, an embodiment herein provides an apparatus for inserting an implant during a surgical procedure, the apparatus comprising a main body comprising a main body shaft comprising a longitudinal channel cavity; and a main body forked end coupled to the main body shaft; an actuator loosely seated within the channel cavity, the actuator comprising an actuator shaft; and an actuator forked end coupled to the actuator shaft; a hinge joint comprising a hinge joint main body coupled to the main body forked end; and a pair of hinge joint arms coupled to the hinge joint main body, wherein each hinge joint arm includes a protruding nipple configured to mate with the implant; an outer sleeve comprising an outer shell surrounding a cavity, wherein the outer sleeve cavity loosely contains the main body, the actuator, and a portion of the hinge joint; a member housing comprising a member housing body comprising a main cavity housing the implant; and a pair of member housing arms coupled to the member housing body; and a linkage component comprising a first linkage end coupled to the actuator forked end; and a second linkage end coupled to at least one of the member housing arms.

In such an apparatus, the main body forked end and the hinged joint main body may each comprise a plurality of coordinating pinholes and the hinge joint main body coupled to the main body forked end through pins securely mated with the coordinating pinholes. In addition, the first linkage end and the actuator forked end may each comprise a plurality of first coordinating pinholes and the first linkage end coupled to the actuator forked end through first pins securely mated with the first coordinating pinholes and the second linkage end and at least one of the member housing arms may each comprise second coordinating pinholes and the second linkage end coupled to at least one of the member housing arms through second pins securely mated with the second coordinating pinholes. Moreover, the actuator loosely may be seated within the channel cavity and is configured to axially move within the channel cavity. Additionally, the implant may rotate upon axially moving the actuator with the channel cavity. Furthermore, the outer sleeve may be configured to move axially with respect to the main body, the actuator, and the hinge joint.

In addition, in such an apparatus, the implant may be secured within the hinge joint upon axially moving the outer sleeve axially with respect to the main body, the actuator, and the hinge joint. Moreover, the implant may be secured within the hinge joint by the outer sleeve pressing the hinge joint arms together upon axially moving the outer sleeve axially with respect to the main body, the actuator, and the hinge joint to thereby securely grip the implant. Furthermore, the linkage may further comprise a curved shaft coupled to the first linkage end and the second linkage end.

Another embodiment herein provides a pivoting insertion apparatus comprising a main body comprising a main body shaft comprising a longitudinal channel cavity; and a main body forked end coupled to the main body shaft; an actuator loosely seated within the channel cavity, the actuator comprising an actuator shaft; and an actuator forked end coupled to the actuator shaft; a hinge joint comprising a hinge joint main body coupled to the main body forked end; and a pair of hinge joint arms coupled to the hinge joint main body, wherein each hinge joint arm includes a protruding nipple; an outer sleeve comprising an outer shell surrounding a cavity, wherein the outer sleeve cavity loosely contains the main body, the actuator, and a portion of the hinge joint; a member housing comprising a member housing body comprising a main cavity; and a pair of member housing arms coupled to the member housing body; a linkage component comprising a first linkage end coupled to the actuator forked end; and a second linkage end coupled to at least one of the member housing arms; and an implant coupled to the member housing, wherein the implant pivots with respect to the hinge joint upon axially moving the actuator within the channel cavity.

In such an apparatus, the main body forked end and the hinged joint main body may each comprise a plurality of coordinating pinholes and the hinge joint main body coupled to the main body forked end through pins securely mated with the coordinating pinholes. In addition, the first linkage end and the actuator forked end may each comprise a plurality of first coordinating pinholes and the first linkage end coupled to the actuator forked end through first pins securely mated with the first coordinating pinholes and the second linkage end and at least one of the member housing arms may each comprise second coordinating pinholes and the second linkage end coupled to at least one of the member housing arms through second pins securely mated with the second coordinating pinholes. Additionally, the outer sleeve may be configured to move axially with respect to the main body, the actuator, and the hinge joint to secure the implant between the pair of hinge joint arms. Furthermore, the linkage may further comprise a curved shaft coupled to the first linkage end and the second linkage end.

In addition, in such an apparatus, the implant may comprises a connecting member comprising a plurality of dimples; and an elongated body outwardly extending from at least one longitudinal end of the connecting member shaft, wherein each dimple is configured to mate the hinge joint arm through the protruding nipple, and wherein the elongated body is configured to mate with an elongation channel. Moreover, the implant may comprise a connecting member comprising a plurality of dimples; and an elongation channel bored within at least one longitudinal end of the connecting member shaft, wherein each dimple is configured to mate the hinge joint arm through the protruding nipple, and wherein the elongation channel is configured to mate with an elongated body. Additionally, the implant comprises an interbody device comprising an interbody device main body; an interbody device attachment body coupled to the interbody main body; and a plurality of dimples, wherein each dimple is configured to mate the hinge joint arm through the protruding nipple. Furthermore, the implant comprises an interbody device comprising an interbody device main body comprising a two opposing side surfaces; an interbody device attachment body coupled to the interbody main body; a pair of textured surfaces, opposing each other and coupled to the interbody device main body; a central cavity centrally bored through the pair of textured surfaces; a plurality of ribbing cavities bored through the side surfaces and forming a plurality of ribs within the side surfaces; and a plurality of dimples, wherein each dimple is configured to mate the hinge joint arm through the protruding nipple.

Another embodiment herein provides a method of articulating a connecting member during surgery, the method comprising providing a connecting member comprising at least one hinge component; providing an insertion device, wherein the pivoting insertion device comprises a main body comprising an actuator loosely connected to the main body; a hinge joint operatively connected to the main body; an outer sleeve operatively connected to the main body; a member housing operatively connected to the main body; and a linkage component operatively connected to the member housing; and actuating the hinge component of the connecting member through the insertion device.

In such a method, actuating the hinge component of the connecting member through the insertion device may comprise rotation of the connecting member along at least one axis of rotation. Moreover, engaging the connecting member to the insertion device may comprise moving the outer sleeve in a first axial direction with respect to the main body, the actuator, and the hinge joint to secure the connecting member; and disengaging the connecting member to the insertion device may comprise moving the outer sleeve in a second axial direction with respect to the main body, the actuator, and the hinge joint to release the connecting member. Furthermore, the at least one hinge component may comprise dimples indented into the connecting member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3 illustrates a schematic diagram of a pivoting insertion apparatus after articulation according to an embodiment herein;

FIG. 4(A) illustrates an enhanced schematic diagram of a pivoting insertion apparatus after articulation according to an embodiment herein;

FIG. 4(B) illustrates another enhanced schematic diagram of a pivoting insertion apparatus after articulation of a curved connecting member according to an embodiment herein;

FIG. 4(C) illustrates an enhanced schematic diagram of a pivoting insertion apparatus after articulation of a first interbody device according to an embodiment herein;

FIG. 4(D) illustrates an enhanced schematic diagram of a pivoting insertion apparatus after articulation of a second interbody device according to an embodiment herein;

FIG. 5(A) illustrates a schematic diagram of a pivoting insertion apparatus after articulation according to an embodiment herein;

FIG. 5(B) illustrates a cross-sectional view of a pivoting insertion apparatus after articulation along the B-B axis of FIG. 5(A) according to an embodiment herein;

FIG. 5(C) illustrates an enhanced cross-sectional view of a pivoting insertion apparatus after articulation along the B-B axis of FIG. 5(A) according to an embodiment herein;

FIG. 6(A) illustrates a schematic diagram of an outer sleeve according to an embodiment herein;

FIG. 6(B) illustrates another schematic diagram of an outer sleeve according to an embodiment herein;

FIG. 6(C) illustrates an cross-sectional schematic diagram of an outer sleeve according to an embodiment herein;

FIG. 6(D) illustrates an enhanced schematic diagram of an outer sleeve according to an embodiment herein;

FIG. 6(E) illustrates a perspective view of an outer sleeve according to an embodiment herein;

FIG. 7(A) illustrates a schematic diagram of a main body according to an embodiment herein;

FIG. 7(B) illustrates another schematic diagram of a main body according to an embodiment herein;

FIG. 7(C) illustrates an enhanced schematic diagram of a main body according to an embodiment herein;

FIG. 7(D) illustrates another enhanced schematic diagram of a main body according to an embodiment herein;

FIG. 7(E) illustrates a cross-sectional schematic diagram of a main body according to an embodiment herein;

FIG. 7(F) illustrates a perspective view of a main body according to an embodiment herein;

FIG. 8(A) illustrates a schematic diagram of an actuator according to an embodiment herein;

FIG. 8(B) illustrates another schematic diagram of an actuator according to an embodiment herein;

FIG. 8(C) illustrates an enhanced schematic diagram of an actuator according to an embodiment herein;

FIG. 8(D) illustrates another enhanced schematic diagram of an actuator according to an embodiment herein;

FIG. 8(E) illustrates a perspective view of an actuator according to an embodiment herein;

FIG. 11(A) illustrates a schematic diagram of a hinge joint according to an embodiment herein;

FIG. 11(B) illustrates another schematic diagram of a hinge joint according to an embodiment herein;

FIG. 11(C) illustrates yet another schematic diagram of a hinge joint according to an embodiment herein;

FIG. 11(D) illustrates a perspective view of a hinge joint according to an embodiment herein;

DETAILED DESCRIPTION OF PREFERRED EMBODIMENTS

Figure 2:
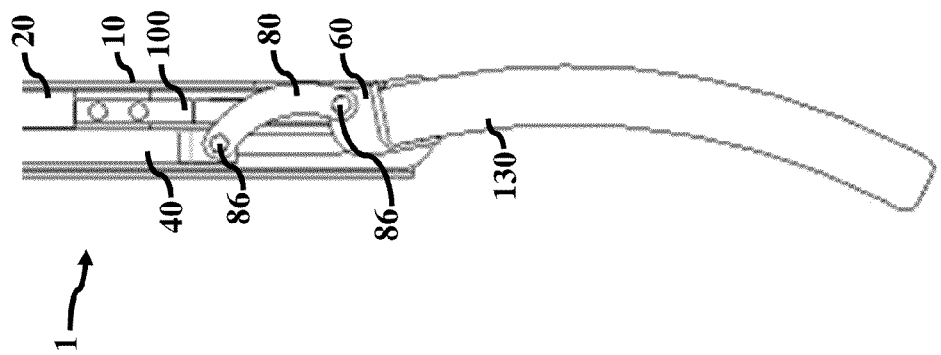
FIG. 2 illustrates an enhanced schematic diagram of the pivoting insertion apparatus in an initial position according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide an apparatus and method to insert a connecting member (e.g., a rod) of a spinal implant during surgery. For example, embodiments herein allow the connecting member to be inserted and rotated inside a limited space. Referring now to the drawings, and more particularly to FIGS. 1 through 13, where similar reference characters denote corresponding features consistently throughout the figures, there are shown preferred embodiments.

Figure 1:
FIG. 1 illustrates a schematic diagram of a pivoting insertion apparatus in an initial position according to an embodiment herein.
Figure 9A:
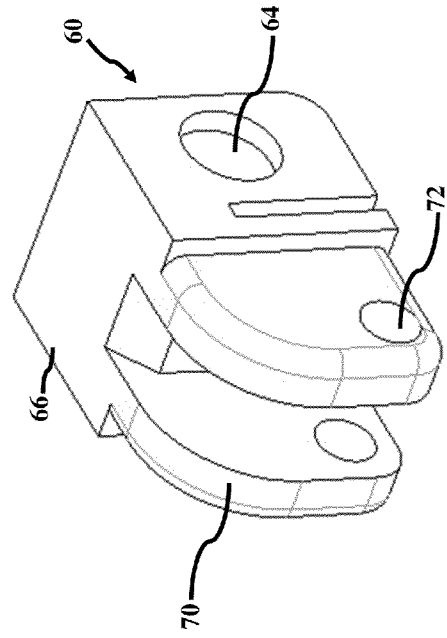
FIG. 9(A) illustrates a schematic diagram of a member housing according to an embodiment herein.
Figure 9B:
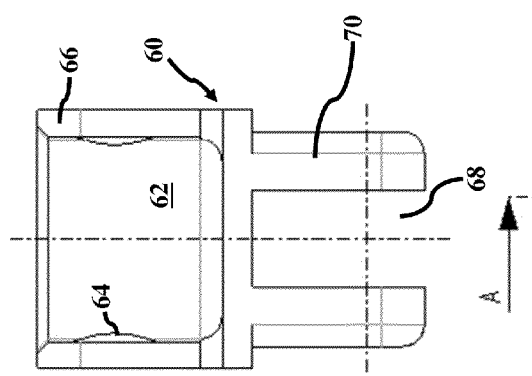
FIG. 9(B) illustrates a perspective view of a member housing according to an embodiment herein.
Figure 9C:
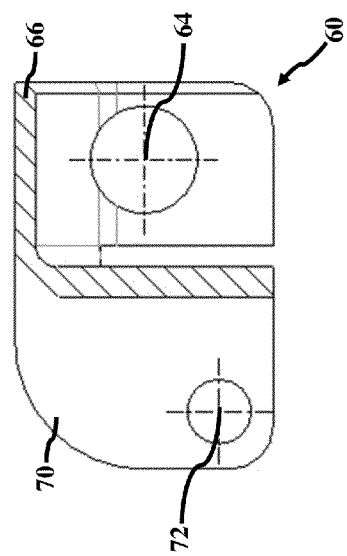
FIG. 9(C) illustrates another schematic diagram of a member housing according to an embodiment herein.
Figure 9D:
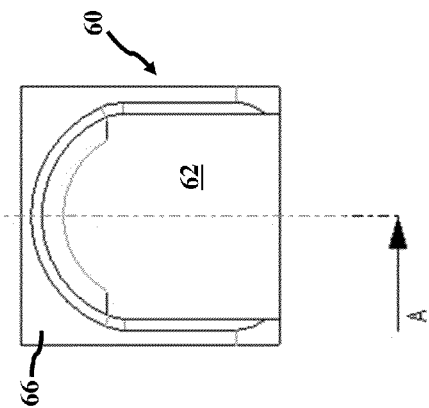
FIG. 9(D) illustrates a cross-sectional view of a member housing along the A-A-A axis of FIG. 9(C) according to an embodiment herein.

FIG. 1 illustrates a schematic diagram of a pivoting insertion apparatus 1 in an initial position according to an embodiment herein. As shown in FIG. 1, pivoting insertion apparatus 1 includes an outer sleeve 10, a main body 20, an actuator 40, linkage 80, and connecting member 130 (e.g., a rod). In addition, FIG. 2 illustrates an enhanced schematic diagram of the pivoting insertion apparatus 1 according to an embodiment herein. Shown in FIG. 2, in addition to the components of pivoting insertion apparatus 1 shown in FIG. 1, are member housing 60, a plurality of pins 86, and hinge joint 100.

In addition, FIG. 3 illustrates a schematic diagram of pivoting insertion apparatus 1 after articulation. As shown in FIG. 3, pivoting insertion apparatus 1 includes an outer sleeve 10, a main body 20, an actuator 40, linkage 80, and connecting member 130. FIG. 4(A) through 4(D) illustrate pivoting insertion apparatus 1 after articulating a variety of attachments according to an embodiment herein. In addition, shown in FIG. 4(A) are additional components of pivoting insertion apparatus 1 that include member housing 60, a plurality of pins 86 and hinge joint 100. In FIGS. 4(B) through 4(D), pivoting insertion apparatus 1 is shown with three separate attachments: curved connecting member 130, first interbody device 130, and second interbody device 150. FIGS. 5(A) through 5(C), with reference to FIGS. 1 through 4(D), also illustrate schematic diagrams of a pivoting insertion apparatus 1 after articulation according to an embodiment herein. Shown in FIG. 5(C), for example, are outer sleeve 10, main body 20, member housing 60, a sectional view of linkage 80, pins 86, connecting member 13, and hinge joint 100—which includes a plurality of arms 102 and protruding nipples 106, as described in further detail below.

As illustrated between FIGS. 1 and 3, actuator 40 moves axially within main body 20. In addition, as shown in FIGS. 2 and 3, linkage 80 is secured (using pin 86) to an end (e.g., forked end 44, shown in FIG. 8(C)) of actuator 40 and is also secured (e.g., using pin 86) to member housing 60. In addition, hinge joint 100 is secured (e.g., using pin 86) to main body 20 at one end (e.g., forked end 24, shown in FIG. 7(D)). As shown in FIG. 5(C), hinge joint 100 is positioned to hold member housing 60 (e.g., between arms 104, shown in FIG. 11(A)).

According to one embodiment herein, as actuator 40 translates axially (shown in FIGS. 1 and 3), linkage 80 and member housing 60 pivot together around hinge joint 100. Such translation, according to one embodiment herein, is due to the fixed location (e.g., attached main body 20) of the hinge joint 100. In addition, as shown in FIGS. 2 and 4(A), connecting member 130 sits within member housing 60 and an attachment mechanism (e.g., a protruding nipple 106 coupled to each arm 104) of hinge joint 100 is inserted into a matching dimple portion (e.g., dimple 134, shown in FIG. 12(B)) of connecting member 130. To secure connecting member 130 to the attachment mechanism of hinge joint 100 (e.g., protruding nipple 106), according to one embodiment herein, outer sleeve 10 is translated axially to thereby squeeze hinge joint 100 (e.g., arms 104) around connecting member 130. Once secured, according to one embodiment herein, actuator 40 articulates (e.g., rotates) connecting member 130. Hinge joint 100 also serves as a pivoting point for the member housing (as shown in FIG. 4(A)) in addition to engaging the connecting member 130 to the member housing 60. Also shown in FIGS.

FIGS. 6(A) through 6(E), with reference to FIGS. 1 through 5(C), illustrate schematic diagrams of outer sleeve 10 according to an embodiment herein. As shown, outer sleeve 10 includes an outer shell 12, surrounding a cavity 13 and terminating into forked end 14. As describe above, according to one embodiment herein, cavity 13 is sufficiently sized to accommodate main body 20 and actuator 40 within itself. In addition, forked end 14 includes a curved cutout 16 and a forked cutout 18. Together, as shown in FIGS. 2 and 4, curved cutout 16 and forked cutout 18 accommodate main body 20, actuator 40, and hinge joint 100 (as shown in FIG. (C)) as well as allowing articulation of connecting member 130 via the pivoting of connecting member 130 around hinge joint 100 and linkage 80.

FIGS. 7(A) through 7(F), with reference to FIGS. 1 through 6(E), illustrate schematic diagrams of main body 20 according to an embodiment herein. As shown, main body 20 includes shaft 22 terminating into forked end 24. Running axially through shaft 22 is cutout channel 26 that, according to one embodiment herein, accommodates actuator 40 within itself. In addition, as shown in FIG. 7(C), forked end 24 includes a first slot 28 and a second slot 30 as well as a plurality of pinholes 32. According to one embodiment herein, first slot 28 provides linear translational motion to pins 86 and second slot 30 provides a passageway to the main body 102. In addition, according to one embodiment herein, pinholes 32 are used to secure hinge joint 100 to main body 20 using a securing mechanism (e.g., pins 86). Moreover, according to one embodiment herein, first slot 28 is longer than second slot 30 (as shown in FIG. 7(C)) and both first slot 28 and second slot 30 are oval-shaped. In addition, forked end 24 includes a first cutout 34 and a second cutout 36—where first cutout 34 forms a pair of arms 38. As shown in FIG. 7(D), according to one embodiment herein, first cutout 34 is larger than second cutout 36 and both first cutout 34 and second cutout 36 are roughly rectangular in shape.

FIGS. 8(A) through 8(E), with reference to FIGS. 1 through 7(F), illustrate schematic diagrams of actuator 40 according to an embodiment herein. As shown, actuator 40 includes a shaft 42 terminating into a forked end 44. In addition, according to one embodiment herein, forked end 44 includes a U-shaped cutout 46 and a pair of arms 48. In addition, according to one embodiment herein, each arm 48 includes a pinhole 50 used to secure linkage 80, as described above, using pin 86.

FIGS. 9(A) through 9(D), with reference to FIGS. 1 through 8(E), illustrate schematic diagrams of member housing 60 according to an embodiment herein. As shown, member housing 60 includes a main cavity 62 to house connecting member 130 inside main body 66—where connecting member 130 is held in place by a pair of nubs 64 protruding from main body 66 into main cavity 62. In addition, member housing 60 includes a cutout 68 flanked by a pair of arms 70. In addition, each arm 70 has a pinhole 72 bored therethrough. According to one embodiment herein, cutout 68 accommodates linkage 80 and linkage 80 is flanked on both sides by arms 70. In addition, according to one embodiment herein, linkage 80 is held in place within cutout 68 by pins 86 inserted through pinholes 72 and pinholes 84 (shown in FIGS. 10(A) and 10(D)).

Figure 10B:
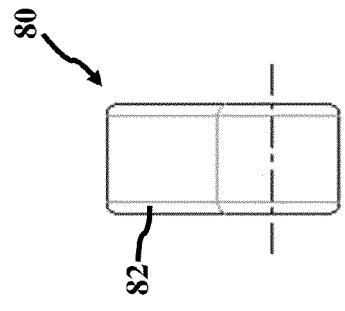
FIG. 10(B) illustrates another schematic diagram of a linkage component according to an embodiment herein.
Figure 10D:
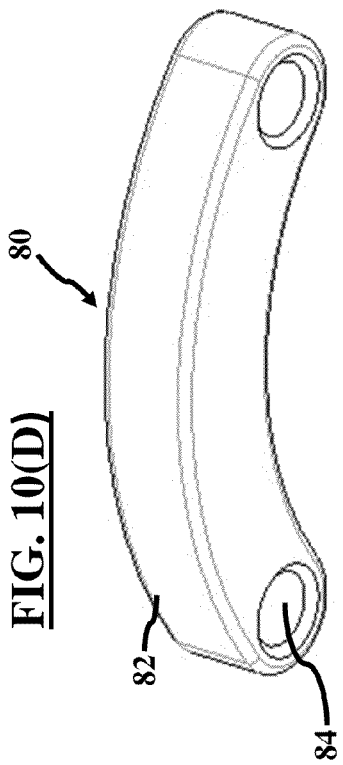
FIG. 10(D) illustrates a perspective view of a linkage component according to an embodiment herein.
Figure 10A:
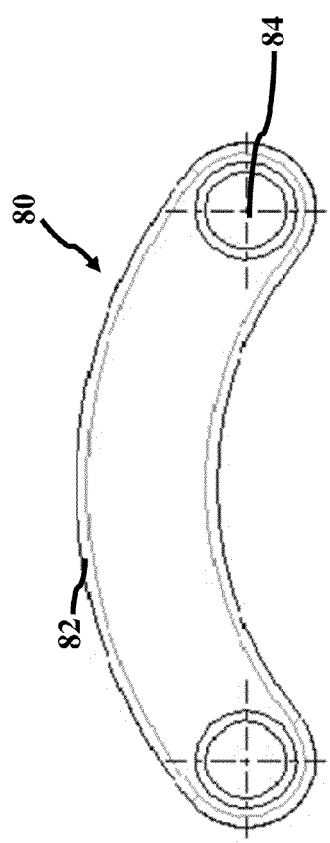
FIG. 10(A) illustrates a schematic diagram of a linkage component according to an embodiment herein.
Figure 10C:
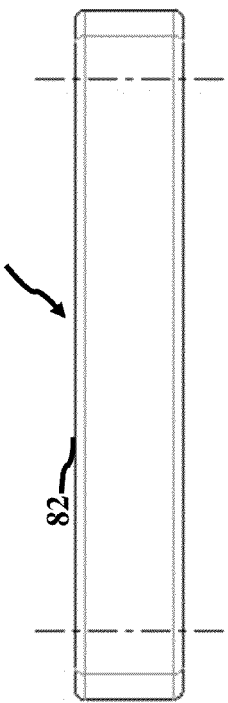
FIG. 10(C) illustrates yet another schematic diagram of a linkage component according to an embodiment herein.

FIGS. 10(A) through 10(D), with reference to FIGS. 1 through 9(D), illustrate schematic diagrams of linkage 80 according to an embodiment herein. As shown, linkage 80 includes a curved shaft 82 and a pinhole 84 at each end. As shown in FIGS. 1 through 4(D), pinholes 86 couple linkage 80 to actuator 40 and member housing 60. In addition, as shown in FIGS. 10(B) and 10(C), one embodiment of linkage 80 has a roughly rectangular cross-section and includes chamfered edges.

FIGS. 11(A) through 11(D), with reference to FIGS. 1 through 10(D), illustrate schematic diagrams of hinge joint 100 according to an embodiment herein. As shown, hinge joint 100 includes main body 102 and a pair of arms 104. At the end of each arm 104, according to one embodiment herein, is a protruding nipple 106. As described above, protruding nipple 106 mates with dimples (e.g., dimples 134, shown in FIG. 12(B)) on connecting member 130. In addition, when outer sleeve 10 slides over arms 104 (and thereby squeezing arms 104 together), connecting member 130 is securely held by hinge joint 100. In addition, main body 102 includes a plurality of pinholes 108 used to couple hinge joint 100 to main body 20.

Figure 12B:
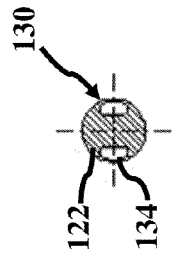
FIG. 12(B) illustrates a cross-sectional schematic diagram of a straight connecting member along the A-A axis according to an embodiment herein.
Figure 12A:
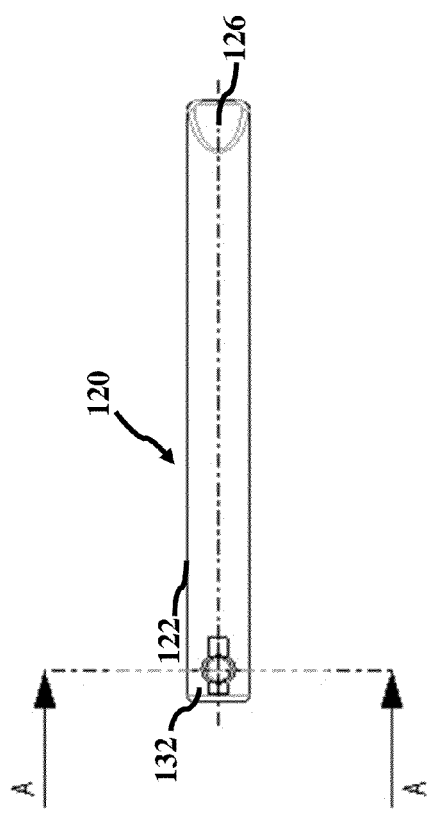
FIG. 12(A) illustrates a schematic diagram of a straight connecting member according to an embodiment herein.
Figure 12D:
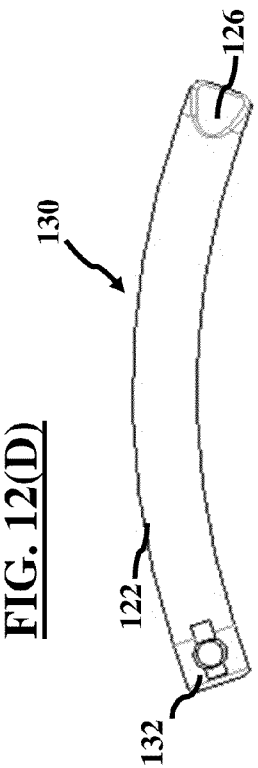
FIG. 12(D) illustrates a schematic diagram of a curved connecting member according to an embodiment herein.
Figure 12C:
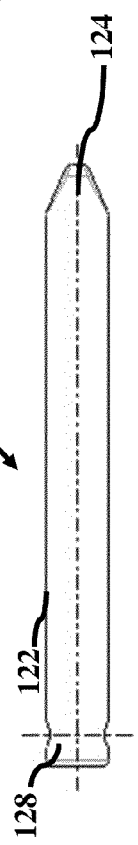
FIG. 12(C) illustrates an alternate schematic diagram of a straight connecting member according to an embodiment herein.
Figure 12H:
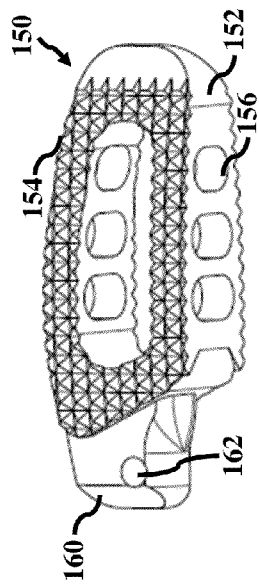
FIG. 12(H) illustrates a schematic diagram of a first view of a second interbody device according to an embodiment herein.
Figure 12I:
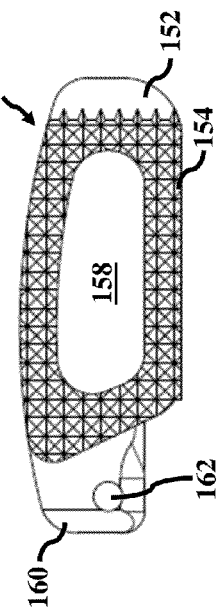
FIG. 12(I) illustrates a schematic diagram of a second view of a second interbody device according to an embodiment herein.
Figure 12J:
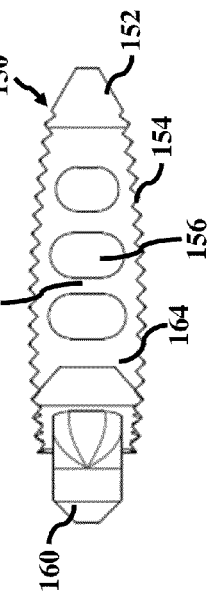
FIG. 12(J) illustrates a schematic diagram of a third view of a second interbody device according to an embodiment herein.
Figure 12E:
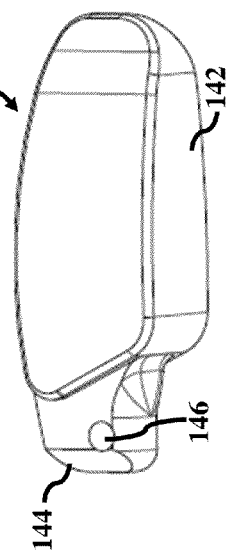
FIG. 12(E) illustrates a schematic diagram of first view of a first interbody device according to an embodiment herein.
Figure 12F:
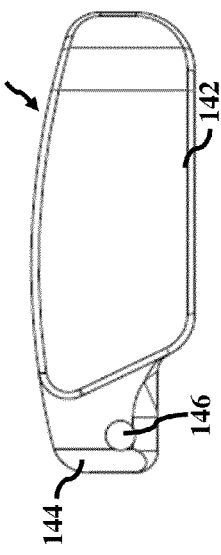
FIG. 12(F) illustrates a schematic diagram of a second view of a first interbody device according to an embodiment herein.
Figure 12G:
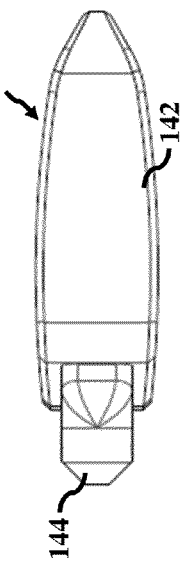
FIG. 12(G) illustrates a schematic diagram of a third view of a first interbody device according to an embodiment herein.

FIGS. 12(A) through 12(C), with reference to FIGS. 1 through 11(D), illustrate schematic diagrams of straight connecting member 120 according to an embodiment herein. In addition, FIG. 12(D) illustrates a schematic diagram of curved connecting member 130 according to an embodiment herein. FIGS. 12(E) through 12(G) illustrate schematic diagrams of first interbody device 140, according to embodiments herein. Moreover, FIGS. 12(H) through 12(J) illustrate a second interbody device 150, according to embodiments herein. As shown, straight connecting member 120 and curved connecting member 130 includes a main body 122 with hinge components (or pivot couplings) 132 cut therein. In addition, according to one embodiment herein, connecting member 120 may include an elongated member 124 or a connecting cavity 126. Similarly, curved connecting member 130 may include an elongated member 124 (not shown) or a connecting cavity 126 (shown in FIG. 12(D)). According to one embodiment herein, hinge components 132 include a plurality of dimples 134 configured to mate with protruding nipples 106 on arms 104 of hinge joint 100. As described above, protruding nipples 106 grip hinge components 132 to temporarily attach connecting member 120 and/or connecting member 130 to pivoting member apparatus 1. In addition, elongated member 124 may mate with connecting cavity 126 on a second end (e.g., connecting end 128 shown in FIG. 12(C), where connecting end 128 includes a cavity (not shown) similar to connecting cavity 126) of a second connecting member 120 and/or connecting member 130 to thereby chain more than one connecting members together. Although connecting member 120 and/or connecting member 130 may be configured as a spinal rod, as shown in FIGS. 12(A) through 12(D); connecting member 120 and connecting member 130 are is not limited to a spinal rod and may include any surgical implant and have any suitable configuration.

For example, interbody device 140 and interbody device 150 may also be used in conjunction with pivoting insertion apparatus 1. As shown in FIGS. 12(E) through 12(G), first interbody device 140 includes a main body 142, an attachment body 144, and a pair of dimples 146. Second interbody device 150, as shown in FIGS. 12(H) through 12(J), includes a main body 152, textured surface 154, a plurality of ribbing cavities 156, a central cavity 158, an attachment body 160, a pair of dimples 162, a side surface 164, and a plurality of ribs 166. As shown in FIG. 4(C), according to one embodiment herein, first interbody device 140 is coupled to pivoting apparatus 1, to allow articulation during surgery, through attachment body 144, which couples with member housing 60 via dimples 146. Similarly, as shown in FIG. 4(D), second interbody device 150 is coupled to pivoting apparatus 1, to allow articulation during surgery, through attachment body 160, which couples with member housing 60 via dimples 162. In addition, second interbody device 160 includes a plurality of ribbing cavities 156 bored into a side surface 164 (where side surface 164 is perpendicular to textured surface 154, according to one embodiment) to form a plurality of ribs 166. In addition, according to one embodiment herein, central cavity 158 is a large cavity bored through the center or textured surface 154.

Figure 13:
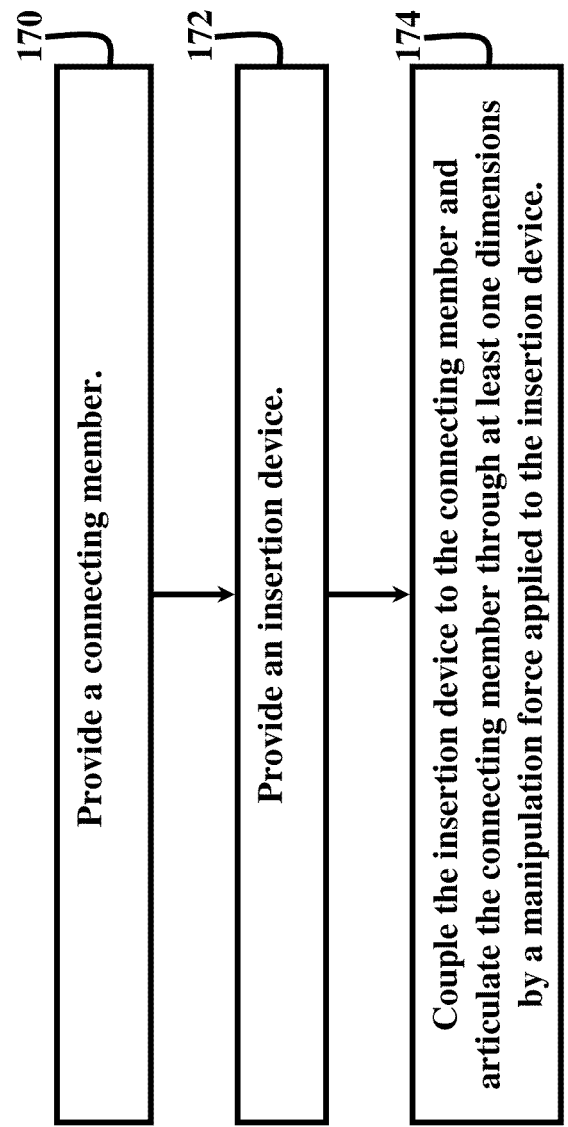
FIG. 13 is a flow diagram illustrating a preferred method according to an embodiment herein.

FIG. 13, with reference to FIGS. 1 through 12(J), illustrates a flow diagram according to an embodiment herein. According to the method shown in FIG. 13, step 170 includes providing a connecting member (e.g., connecting member 120, connecting member 130, first interbody device 140, and/or second interbody device 150, shown in FIGS. 12(A) through 12(J)). Step 172 includes providing an insertion device (e.g., pivoting insertion apparatus 1, shown in FIGS. 1 through 5(C)). Next, in step 174, the method shown in FIG. 13 couples the insertion device to the connecting member and articulates the connecting member through at least one dimensions by a manipulation force applied to the insertion device (e.g., movement of connecting member 130 from and initial position to a position after articulation, as shown in FIGS. 1 through 4(D)).

As described above, the embodiments herein are applicable to a wide variety of applications and provide an apparatus and method to insert a connecting member of the spinal implant during surgery. For example, during minimally invasive surgical techniques (e.g., for spinal and neurosurgical applications), embodiments herein allow the connecting member to be inserted and rotated inside the limited space.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An apparatus for inserting an implant during a surgical procedure, said apparatus comprising:
a main body comprising:
a main body shaft comprising a longitudinal channel cavity; and
a main body forked end coupled to said main body shaft;
an actuator loosely seated within said channel cavity, wherein said actuator is configured to axially move within said channel cavity, said actuator comprising:
an actuator shaft; and
an actuator forked end coupled to said actuator shaft;
a hinge joint comprising:
a hinge joint main body coupled to said main body forked end; and
a pair of hinge joint arms coupled to said hinge joint main body, wherein each hinge joint arm includes a protruding nipple configured to mate with said implant;
an outer sleeve comprising an outer shell surrounding a cavity, wherein said outer sleeve cavity loosely contains said main body, said actuator, and a portion of said hinge joint;
a member housing comprising:
a member housing body comprising a main cavity housing said implant; and
a pair of member housing arms coupled to said member housing body; and
a linkage component comprising:
a first linkage end coupled to said actuator forked end; and
a second linkage end coupled to at least one of said member housing arms.

2. The apparatus of claim 1, wherein said main body forked end and said hinged joint main body each comprise a plurality of coordinating pinholes and said hinge joint main body is coupled to said main body forked end through pins securely mated with said coordinating pinholes.

3. The apparatus of claim 1,
wherein said first linkage end and said actuator forked end each comprise a plurality of first coordinating pinholes and said first linkage end is coupled to said actuator forked end through first pins securely mated with said first coordinating pinholes, and
wherein said second linkage end and at least one of said member housing arms each comprise second coordinating pinholes and said second linkage end is coupled to at least one of said member housing arms through second pins securely mated with said second coordinating pinholes.

4. The apparatus of claim 1, wherein said implant rotates upon axially moving said actuator within said channel cavity.

5. The apparatus of claim 1, wherein said outer sleeve is configured to move axially with respect to said main body, said actuator, and said hinge joint.

6. The apparatus of claim 5, wherein said implant is secured within said hinge joint upon axially moving said outer sleeve axially with respect to said main body, said actuator, and said hinge joint.

7. The apparatus of claim 6, wherein said implant is secured within said hinge joint by said outer sleeve pressing said hinge joint arms together upon axially moving said outer sleeve axially with respect to said main body, said actuator, and said hinge joint to thereby securely grip said implant.

8. An apparatus for inserting an implant during a surgical procedure, said apparatus comprising:
a main body comprising:
a main body shaft comprising a longitudinal channel cavity; and
a main body forked end coupled to said main body shaft;
an actuator loosely seated within said channel cavity, said actuator comprising:
an actuator shaft; and
an actuator forked end coupled to said actuator shaft;
a hinge joint comprising:
a hinge joint main body coupled to said main body forked end; and
a pair of hinge joint arms coupled to said hinge joint main body, wherein each hinge joint arm includes a protruding nipple configured to mate with said implant;
an outer sleeve comprising an outer shell surrounding a cavity, wherein said outer sleeve cavity loosely contains said main body, said actuator, and a portion of said hinge joint;

a member housing comprising:
  a member housing body comprising a main cavity housing said implant; and
  a pair of member housing arms coupled to said member housing body; and
a linkage component comprising:
  a first linkage end coupled to said actuator forked end;
  a second linkage end coupled to at least one of said member housing arms; and
  a curved shaft coupled to said first linkage end and said second linkage end.

9. The apparatus of claim 8,
wherein said implant comprises a connecting member comprising:
  a plurality of dimples; and
  an elongated body outwardly extending from at least one longitudinal end of said connecting member,
wherein each dimple is configured to mate said hinge joint arm through said protruding nipple, and
wherein said elongated body is configured to mate with an elongation channel.

10. The apparatus of claim 8,
wherein said implant comprises a connecting member comprising:
  a plurality of dimples; and
  an elongation channel bored within at least one longitudinal end of said connecting member,
wherein each dimple is configured to mate said hinge joint arm through said protruding nipple, and
wherein said elongation channel is configured to mate with an elongated body.

11. The apparatus of claim 8,
wherein said implant comprises an interbody device comprising:
  an interbody device main body;
  an interbody device attachment body coupled to said interbody main body; and
  a plurality of dimples,
wherein each dimple is configured to mate said hinge joint arm through said protruding nipple.

12. The apparatus of claim 8,
wherein said implant comprises an interbody device comprising:
  an interbody device main body comprising two opposing side surfaces;
  an interbody device attachment body coupled to said interbody main body;
  a pair of textured surfaces, opposing each other and coupled to said interbody device main body;
  a central cavity centrally bored through said pair of textured surfaces;
  a plurality of ribbing cavities bored through said side surfaces and forming a plurality of ribs within said side surfaces; and
  a plurality of dimples,
wherein each dimple is configured to mate said hinge joint arm through said protruding nipple.

13. A pivoting insertion apparatus comprising:
a main body comprising:
  a main body shaft comprising a longitudinal channel cavity; and
  a main body forked end coupled to said main body shaft;
an actuator loosely seated within said channel cavity, said actuator comprising:
  an actuator shaft; and
  an actuator forked end coupled to said actuator shaft;
a hinge joint comprising:
  a hinge joint main body coupled to said main body forked end; and
  a pair of hinge joint arms coupled to said hinge joint main body, wherein each hinge joint arm includes a protruding nipple;
an outer sleeve comprising an outer shell surrounding a cavity, wherein said outer sleeve cavity loosely contains said main body, said actuator, and a portion of said hinge joint;
a member housing comprising:
  a member housing body comprising a main cavity; and
  a pair of member housing arms coupled to said member housing body;
a linkage component comprising:
  a first linkage end coupled to said actuator forked end; and
  a second linkage end coupled to at least one of said member housing arms; and
an implant coupled to said member housing, wherein said implant pivots with respect to said hinge joint upon axially moving said actuator within said channel cavity,
wherein said main body forked end and said hinged joint main body each comprise a plurality of coordinating pinholes and said hinge joint main body is coupled to said main body forked end through pins securely mated with said coordinating pinholes.

14. The pivoting insertion apparatus of claim 13,
wherein said first linkage end and said actuator forked end each comprise a plurality of first coordinating pinholes and said first linkage end is coupled to said actuator forked end through first pins securely mated with said first coordinating pinholes, and
wherein said second linkage end and at least one of said member housing arms each comprise second coordinating pinholes and said second linkage end is coupled to at least one of said member housing arms through second pins securely mated with said second coordinating pinholes.

15. The pivoting insertion apparatus of claim 13,
wherein said implant comprises a connecting member comprising:
  a plurality of dimples; and
  an elongated body outwardly extending from at least one longitudinal end of said connecting member,
wherein each dimple is configured to mate said hinge joint arm through said protruding nipple, and
wherein said elongated body is configured to mate with an elongation channel.

16. The pivoting insertion apparatus of claim 13,
wherein said implant comprises a connecting member comprising:
  a plurality of dimples; and
  an elongation channel bored within at least one longitudinal end of said connecting member,
wherein each dimple is configured to mate said hinge joint arm through said protruding nipple, and
wherein said elongation channel is configured to mate with an elongated body.

17. The pivoting insertion apparatus of claim 13,
wherein said implant comprises an interbody device comprising:
  an interbody device main body;
  an interbody device attachment body coupled to said interbody main body; and
  a plurality of dimples, wherein each dimple is configured to mate said hinge joint arm through said protruding nipple.

18. The pivoting insertion apparatus of claim 13, wherein said implant comprises an interbody device comprising:
   an interbody device main body comprising two opposing side surfaces;
   an interbody device attachment body coupled to said interbody main body;
   a pair of textured surfaces, opposing each other and coupled to said interbody device main body;
   a central cavity centrally bored through said pair of textured surfaces;
   a plurality of ribbing cavities bored through said side surfaces and forming a plurality of ribs within said side surfaces; and
   a plurality of dimples,
wherein each dimple is configured to mate said hinge joint arm through said protruding nipple.

19. A pivoting insertion apparatus comprising:
a main body comprising:
   a main body shaft comprising a longitudinal channel cavity; and
   a main body forked end coupled to said main body shaft;
an actuator loosely seated within said channel cavity, said actuator comprising:
   an actuator shaft; and
   an actuator forked end coupled to said actuator shaft;
a hinge joint comprising:
   a hinge joint main body coupled to said main body forked end; and
   a pair of hinge joint arms coupled to said hinge joint main body, wherein each hinge joint arm includes a protruding nipple;
an outer sleeve comprising an outer shell surrounding a cavity, wherein said outer sleeve cavity loosely contains said main body, said actuator, and a portion of said hinge joint;
a member housing comprising:
   a member housing body comprising a main cavity; and
   a pair of member housing arms coupled to said member housing body;
a linkage component comprising:
   a first linkage end coupled to said actuator forked end; and
   a second linkage end coupled to at least one of said member housing arms; and
an implant coupled to said member housing, wherein said implant pivots with respect to said hinge joint upon axially moving said actuator within said channel cavity,
wherein said outer sleeve is configured to move axially with respect to said main body, said actuator, and said hinge joint to secure said implant between said pair of hinge joint arms.

20. The pivoting insertion apparatus of claim 19, wherein said implant comprises a connecting member comprising:
   a plurality of dimples; and
   an elongated body outwardly extending from at least one longitudinal end of said connecting member,
wherein each dimple is configured to mate said hinge joint arm through said protruding nipple, and
wherein said elongated body is configured to mate with an elongation channel.

21. A pivoting insertion apparatus comprising:
a main body comprising:
   a main body shaft comprising a longitudinal channel cavity; and
   a main body forked end coupled to said main body shaft;
an actuator loosely seated within said channel cavity, said actuator comprising:
   an actuator shaft; and
   an actuator forked end coupled to said actuator shaft;
a hinge joint comprising:
   a hinge joint main body coupled to said main body forked end; and
   a pair of hinge joint arms coupled to said hinge joint main body, wherein each hinge joint arm includes a protruding nipple;
an outer sleeve comprising an outer shell surrounding a cavity, wherein said outer sleeve cavity loosely contains said main body, said actuator, and a portion of said hinge joint;
a member housing comprising:
   a member housing body comprising a main cavity; and
   a pair of member housing arms coupled to said member housing body;
a linkage component comprising:
   a first linkage end coupled to said actuator forked end;
   a second linkage end coupled to at least one of said member housing arms; and
   a curved shaft coupled to said first linkage end and said second linkage end; and
an implant coupled to said member housing, wherein said implant pivots with respect to said hinge joint upon axially moving said actuator within said channel cavity.

22. The pivoting insertion apparatus of claim 21, wherein said implant comprises a connecting member comprising:
   a plurality of dimples; and
   an elongated body outwardly extending from at least one longitudinal end of said connecting member,
wherein each dimple is configured to mate said hinge joint arm through said protruding nipple, and
wherein said elongated body is configured to mate with an elongation channel.

\* \* \* \* \*